US008753660B2

(12) United States Patent
Behnam et al.

(10) Patent No.: US 8,753,660 B2
(45) Date of Patent: Jun. 17, 2014

(54) ACTIVATING EXTRACTION OF DEMINERALIZED BONE MATRIX

(75) Inventors: Keyvan Behnam, Red Bank, NJ (US); Elsa J. Brochmann-Murray, Saugus, CA (US); Samuel S. Murray, Saugus, CA (US)

(73) Assignees: The Regents of The University of California, Oakland, CA (US); The United States of America as Represented by The Department of Veterans Affairs, Washington, DC (US)

( * ) Notice: Subject to any disclaimer, the term of this patent is extended or adjusted under 35 U.S.C. 154(b) by 1200 days.

(21) Appl. No.: 11/791,940

(22) PCT Filed: Nov. 29, 2005

(86) PCT No.: PCT/US2005/043215
§ 371 (c)(1),
(2), (4) Date: Feb. 11, 2008

(87) PCT Pub. No.: WO2006/093545
PCT Pub. Date: Sep. 8, 2006

(65) Prior Publication Data
US 2008/0268012 A1    Oct. 30, 2008

Related U.S. Application Data

(60) Provisional application No. 60/631,334, filed on Nov. 29, 2004.

(51) Int. Cl.
*A61K 35/32* (2006.01)
(52) U.S. Cl.
USPC .......... 424/423; 424/682; 424/676; 424/93.7; 424/549; 514/21; 514/12; 623/11.11
(58) Field of Classification Search
None
See application file for complete search history.

(56) References Cited

U.S. PATENT DOCUMENTS

| | | | |
|---|---|---|---|
| 4,789,732 A | 12/1988 | Urist | |
| 4,843,063 A | 6/1989 | Seyedin et al. | |
| 5,158,934 A | 10/1992 | Ammann et al. | |
| 5,393,739 A | 2/1995 | Bentz et al. | |
| 5,407,810 A * | 4/1995 | Builder et al. | 435/69.1 |
| 5,620,867 A | 4/1997 | Kiefer et al. | |
| 5,981,483 A | 11/1999 | Dennis et al. | |
| 6,200,606 B1 | 3/2001 | Peterson et al. | |
| 6,291,428 B1 | 9/2001 | Macaulay et al. | |
| 6,311,690 B1 | 11/2001 | Jefferies | |
| 6,322,786 B1 | 11/2001 | Anderson | |
| 7,241,874 B2 * | 7/2007 | Thorne | 530/412 |
| 8,188,219 B2 | 5/2012 | Murray et al. | |
| 8,193,312 B2 | 6/2012 | Murray et al. | |
| 8,415,302 B2 | 4/2013 | Murray et al. | |
| 2003/0095993 A1 | 5/2003 | Bentz et al. | |
| 2006/0270645 A1 | 11/2006 | Parhami | |
| 2007/0056050 A1 | 3/2007 | Clokie et al. | |
| 2007/0065415 A1 | 3/2007 | Kleinsek et al. | |
| 2008/0234219 A1 | 9/2008 | Brunkow et al. | |
| 2008/0241108 A1 | 10/2008 | Murray et al. | |
| 2008/0268012 A1 | 10/2008 | Behnam et al. | |
| 2009/0047360 A1 | 2/2009 | Murray et al. | |
| 2013/0095075 A1 | 4/2013 | Murray et al. | |
| 2013/0303449 A1 | 11/2013 | Murray et al. | |

FOREIGN PATENT DOCUMENTS

| | | |
|---|---|---|
| EP | 0409472 | 1/1991 |
| JP | 4235197 A | 8/1992 |
| JP | 5085939 A | 4/1993 |
| JP | H09505305 A | 5/1997 |
| WO | WO9621006 A1 | 7/1996 |
| WO | WO9731661 A1 | 9/1997 |
| WO | WO9740137 A1 | 10/1997 |
| WO | WO2004004630 A2 | 1/2004 |
| WO | WO2004013294 A2 | 2/2004 |
| WO | WO2004097424 A1 | 11/2004 |
| WO | WO2005/072403 | 8/2005 |
| WO | WO2006/093545 | 9/2006 |
| WO | WO2008/079400 | 8/2008 |
| WO | WO2009067177 A2 | 5/2009 |

OTHER PUBLICATIONS

Urist et al ("Purification of bovine bone morphogenetic protein by hydroxyapatite chromatography," PNS 81: 371-375 (1984).*
Behnam et al ("Alkali-Urea Extraction of Demineralized Bone Matrix Removes Noggin, an Inhibitor of Bone Morphogenetic Proteins," Connective Tissue Research 45: 257-260 (2004).*
Urist, et al., Purification of bovine bone morphogenetic protein by hydroxyapatite chromatography, Proc. Natl. Acad. Sci. USA 81:371-375 (1984).*
Behnam, et al. "Identification of the Molecular Chaperon Alpa B-Crystallin in Demineralized Bone Powder and Osteoblast-Like Cells." Journal of Orthopaedic Research, vol. 20(6), pp. 1190 (Nov. 2002).
Behnam, et al. "BMP Binding Peptide: a BMP-2 Enhancing Factor Deduced From the Sequence of Native Bovine Bone Morphogenetic Protein/Non-Collagenous Protein." Journal of Orthopaedic Research, vol. 23, pp. 175-180 (2005).
Brown, et al. "Friends and Relations of the Cystatin Superfamily-new members and Their Evolution." Protein Science, vol. 6, pp. 5-12 (1987).

(Continued)

*Primary Examiner* — Suzanne Ziska
(74) *Attorney, Agent, or Firm* — McDermott Will & Emery LLP

(57) ABSTRACT

Demineralized bone matric (DBM) and native bone morphogenetic protein (nBMP) are complex mixtures of non-collagenous bone proteins. These mixtures contain many of the BMPs that are available as recombinant molecules. Information regarding the presence in these materials of molecules that may affect the availability and activity of the BMPs is very limited. A chemical extraction of DBM, such as using alkali-urea produces a water soluble extractate which inhibits the osteogenic activity of DBM. Noggin, an extracellular BMP ligand antagonist is found in the water soluble extractate from DBM. Differential chemical extraction is a useful means of removing non-osteogenic, or osteogenic inhibitory molecules from DBM and nBMP.

8 Claims, 4 Drawing Sheets

(56) References Cited

OTHER PUBLICATIONS

Carano, et al. "Angiogenesis and Bone Repair." Drug Discovery Today, vol. 8(21), pp. 980-989 (Nov. 2003).
Demetriou, et al. "Fetuin/α2-HS Glycoprotein Is a Transforming Growth Factor-β Type II Receptor Mimic and Cytokin Antagonist." Journal of Biological Chemistry, vol. 271(22), pp. 12755-12761 (May 1996).
Hu, et al. "Isolation and Molecular Cloning of a Novel Bone Phosphoprotein Related in Sequence to the Cystatin Family of Thiol Protease Inhibitors." Journal of Biological Chemistry, vol. 270(1), pp. 431-436 (Jan. 1995).
Miller-Bertoglio, et al. "Maternal and Zygotic Activity of the Zebrafish *ogon* Locus Antagonizes BMP Signaling." Developmental Biology, vol. 214, pp. 72-89 (1999).
Murray, et al. "Strain-Dependent Differences in Vertebral Bone Mass, Serum Osteocalcin, and Calcitonin in Calcium-Replete and -Deficient Mice." Pro. Soc. Exp. Biol. Med., vol. 203, pp. 64-73 (1993).
Notredame, et al. "T-Coffee: A Novel Method for Fast and Accurate Multiple Sequence Alignment." Journal of Molecular Biology, vol. 302, pp. 205-217 (2000).
Parfitt, et al. "Bone Histomorphometry: Standardization of Nomenclature, Symbols, and Units." Journal of Bone and Mineral Research, vol. 2(6) pp. 595-610 (1987).
Ten Dijke, et al. "Controlling Cell Fate by Bone Morphogenetic Protein Receptors." Molecular and Cellular Endrocrinology. vol. 211, pp. 105-113 (2003).
Urist, "Bone: Formation by Autoinduction." Science, vol. 150, pp. 893-899 (Nov. 1965).
Urist, "Emerging Concepts of Bone Morphogenetic Protein." Fundamentals of Bone Growth: Methodology and Applications, pp. 189-198 (1991).
Urist, et al. "Preparation and Bioassay of Bone Morphogenic Protein and Polypeptide Fragments." Methods in Enzymology, vol. 146, pp. 294-312 (1987).
Urist, et al., "Purification of Bovine Bone Morphogenetic Protein by Hydroxyapatite Chromatography." Proc. Natl. Acad. Sci. USA, vol. 81, pp. 371-375 (Jan. 1984).
Urist, et al. "Hydroxyapatite Affinity, Electroelution, and Radioimmunoassay for Identification of Human and Bovine Bone Morphogenetic Proteins and Polypeptides." Development and Diseases of Cartilage and Bone Matrix, pp. 149-176 (1987).
Zhoa, et al. "Targeted Overexpression of Insulin-Like Growth Factor I to Osteoblasts of Transgenic Mice: Increased Trabecular Bone Volume Without Increased Osteoblast Proliferation." Endocrinology, vol. 141(7), pp. 2674-2682 (2000).
International Search Report and Written Opinion for PCT/US2005/002722 dated Dec. 19, 2005.
International Search Report and Written Opinion for PCT/US2005/043215 dated Aug. 3, 2006.
International Search Report and Written Opinion for PCT/US2007/026315 dated Jun. 17, 2008.
Behnam, et al. "Alkali-urea Extraction of Demineralized Bone Matrix Removes Noggin, an Inhibitor of Bone Morphogenetic Proteins." Connective Tissue Research 2004,, vol. 45, No. 4-5, pp. 257-260 (Jul. 2004).
Sampath, et al. "Dissociative Extraction and Reconstitution of Extracellular Matrix Component involved in Local Bone Differentiation." Proceedings of the National Academy of Sciences of USA, vol. 78, No. 12, pp. 7599-7603 (Dec. 1981).
Takahashi "[Bone Morphogenetic Protein (BMP): From Basic Studies to Clinical Approaches]." Nippon Yakurigaku Zasshi. Folia Pharmacologica Japonica, vol. 116, No. 4, pp. 232-240 (Oct. 2000).
Ripamonti, et al. "Xenogeneic Osteogenin a Bone Morphogenetic Protein and Demineralized Bone Matrices Including Human Induce Bone Differentiation in Athymic Rats and Baboons." Matrix: Collagen and Related Research, vol. 11, No. 6, pp. 404-411 (Jan. 1991).
Chen, et al. "Bone Morphogenetic Proteins" Growth Factors, vol. 22, No. 4, pp. 233-241 (Dec. 2004).
Supplementary European Search Report for EP05857032 dated Aug. 7, 2009.
International Search Report and Written Opinion for PCT/US2008/012833 dated May 4, 2009.
Search Report for European Patent Application No. 07868028 dated Jul. 6, 2011.
Search Report for European Patent Application No. 08852773 dated Jul. 6, 2011.
Search Report for European Patent Application No. 10797441 dated Jun. 21, 2013.
Bender, et al. "Sickle Cell Disease." NCBI Bookshelf. A service of the National Library of Medicine, National Institutes of Health, 1993-2013, Bookshelf ID: NBK1377PMID: 20301551.
Bennett, et al. "Characterization of the Human Secreted Phosphoprotein 24 Gene (SPP2) and Comparison of the Protein Sequence in Nine Species." Matrix Biology, vol. 22, No. 8, pp. 641-651 (2004).
Bowie, et al. "Deciphering the Message in Protein Sequences: Tolerance to Amino Acid Substitutions." Science, vol. 247, Mar. 16, 1990, pp. 1306-1310.
Guo, et al. "Protein Tolerance to Random Amino Acid Change." Proc. Natl. Acad. Sci. U.S.A. Jun. 22, 2004; 101(25):9205-10.
Herrera-Esparza, et al. "An Activin Receptor IA/Activin-Like Kinase-2 (R206H) Mutation in Fibrodysplasia Ossificans Progressiva." Hindawi Publishing Corporation Case Reports in Genetics, vol. 2013, Article ID 260371 (2013).
Madian, et al. "Effect of Single Amino Acid Substitution on Oxidative Modifications of the Parkinson's Disease-Related Protein, DJ-1." Molecular & Cellular Proteomics 11.2 (2012).
Mamidi, et al. "Alanine or aspartic acid substitutions at serine23/24 of cardiac troponin I decrease thin filament activation, with no effect on crossbridge detachment kinetics." Arch Biochem Biophys., vol. 525 (2012).
Murray, et al. "Recombinant Expression, Isolation, and Proteolysis of Extracellular Matrix-Secreted Phosphoprotein-24 kDa." Connect Tissue Res. 2007; 48(6):292-9.
Ngo, et al. "Computational Complexity, Protein Structure Prediction, and the Levinthal Paradox." The Protein Folding Problem and Tertiary Structure Prediction, Aug. 1994, Springer Verlag, pp. 433 and 492-495.
Perron, et al. "Structural distinctions in BMPs underlie divergent signaling in spinal neurons." Neural Development, 7:16 (2012).
Sintuu, et al. Full-Length Bovine spp24 [spp24 (24-203)] Inhibits BMP-2 Induced Bone Formation. Journal of Orthopaedic Research, Jun. 2008, pp. 753-758.
Sintuu, et al. "Full-Length spp24, but Not Its 18.5-kDa Proteolytic Fragment, Inhibits Bone-Healing in a Rodent Model of Spine Fusion." Journal of Bone and Joint Surgery, vol. 93-A, No. 11, pp. 1022-1032 (2011).

\* cited by examiner

FIG. 1
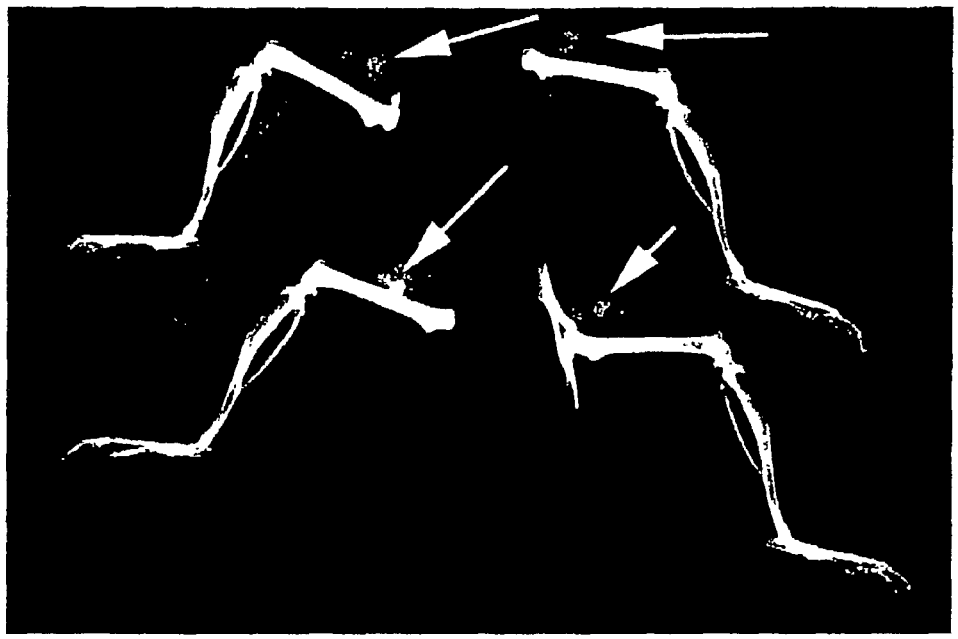
DMB        Extracted DMB
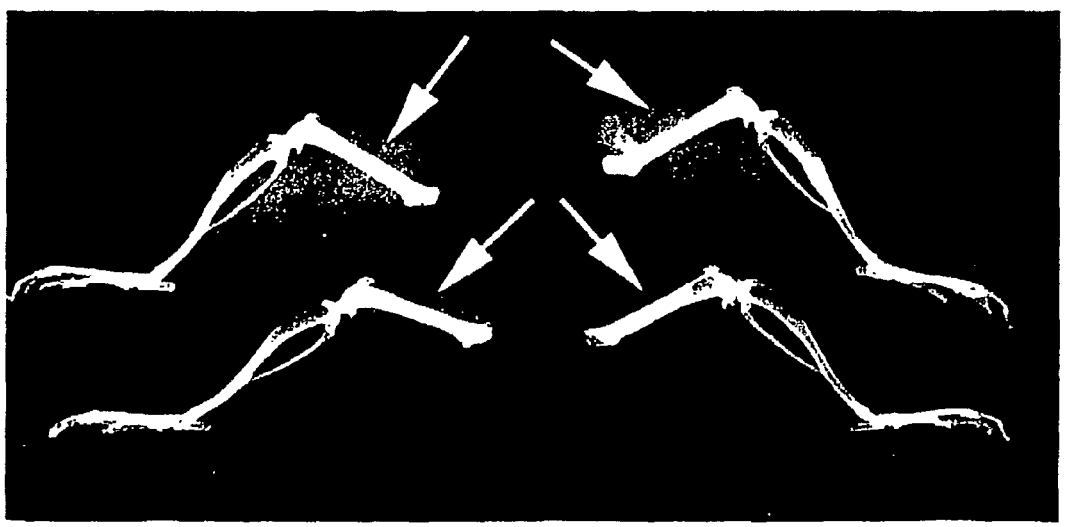
FIG. 2

ACTIVATING EXTRACTION OF DEMINERALIZED BONE MATRIX

This application claims priority from International Patent Application No. PCT/US2005/043215, filed Nov. 29, 2005, which claims priority to U.S. Provisional Patent Application No. 60/631,334, filed Nov. 29, 2004, both of which are incorporated by reference herein.

STATEMENT REGARDING FEDERALLY SPONSORED RESEARCH OR DEVELOPMENT

This work was supported by the Department of Veterans' Affairs. The United States government may have certain rights in the invention.

FIELD OF THE INVENTION

The invention generally relates to osteogenic factors, and more particularly to demineralized bone matrix ("DBM") and/or native bone morphogenetic protein ("nBMP"), to compositions including DBM and/or nBMP having at least one endogenous inhibitor of osteogenic activity removed therefrom, articles of manufacture including DBM and/or nBMP and methods of using the compositions and articles to induce osteogenesis.

BACKGROUND OF THE INVENTION

Normal bone formation occurs during development and repair after injury and remodeling occurs in adult life to preserve the integrity of the skeleton. Bone formation and remodeling generally involve bone resorption by osteoclasts and bone formation by osteoblasts, which are regulated by growth factors. Thus, any interference between the balance in cell differentiation, bone formation and bone resorption can affect bone formation, repair and homeostasis.

Noggin is a protein which is present and highly conserved in both protostome and deuterstome phyla and which interacts with bone mophogenic proteins ("BMPs") to affect embryonic orientation and tissue layer formation in early development. (Reddi, A. H. (2001). Interplay between bone morphogenetic proteins and cognate binding proteins in bone and cartilage development: noggin, chordin and DAN. Arthritis Res. 3:1-5. Zimmerman; L. B., et al. (1996) The Spemann organizer signal noggin binds and inactivates bone morphogenetic protein 4. Cell 86:599-606.) It is a 33 kD glycoprotein which is secreted as a 64 kD homodimer and was shown to perform the functions of the active principle of the Spemann organizer in *Xenopus* in that it induced neural tissue from dorsal ectoderm and changed the specification of lateral mesoderm from ventral (blood, mesenchyme) to dorsal (muscle, heart, pronephros) fates during gastrulation (Smith, W. C., et al. (1993). Secreted noggin protein mimics the Spemann organizer in dorsalizing *Xenopus* mesoderm. Nature 361:547-549. Lamb, T. M., et al. (1993) Neural induction by the secreted polypeptide noggin. Science 262:713-718). BMP-4 had been demonstrated to act as a ventralizing factor in *Xenopus* development (Dale, L., et al. (1992) Bone morphogenetic protein 4: a ventralizing factor in early *Xenopus* development. Development 115:573-585. Jones, C. M., et al. (1992) DVR-4 (bone morphogenetic protein-4) as a posterior-ventralizing factor in *Xenopus* mesoderm induction. Development 115:639-647) and to inhibit neural induction (Wilson, P. A., and Hemmati-Brivanlou, A. (1995) Induction of epidermis and inhibition of neural fate by BMP 4. Nature 376:331-333) suggesting that noggin may function by interacting with BMP-4. Subsequent studies demonstrated that noggin avidly binds BMP-4 and inhibits its activity by blocking binding of BMP-4 to cellular receptors (Zimmerman, L. B., et al. (1996) The Spemann organizer signal noggin binds and inactivates bone morphogenetic protein 4. Cell 86:599-606. Groppe, J., Greenwald, J., et al. (2002) Structural basis of BMP signaling inhibition by the cystein knot protein noggin. Nature 420:636-642).

Noggin performs important regulatory functions in the vertebrate skeleton (Brunet, L. J., et al. (1998) Noggin, cartilage morphogenesis, and joint formation in the mammalian skeleton. Science 280:1455-1457. Devlin, R. D., et al. (2003) Skeletal over expression of noggin results in osteopenia and reduced bone formation. Endocrinology 144:1972-1978. Nakamura, Y., Wakitani, S., Nakayama, J., et al. (2003) Temporal and spatial expression profiles of BMP receptors and noggin during bmp-2-induced ectopic bone formation. J. Bone Min. Res. 18:1854-1862. Stottmann, R. W., et al. (2001) The BMP antagonists chordin and noggin have essential but redundant roles in mouse mandibular outgrowth. Dev. Biol. 240:457-473). Noggin reduced BMP-4-induced expression of alkaline phosphatase in W-20-17 mouse bone marrow stromal cells, which were isolated on the basis of manifesting an osteoblast-like phenotype after treatment with rhBMP-2 (Theis, R. S., et al. (1992) Recombinant human bone morphogenetic protein-2 induces osteoblastic differentiation in W-20-17 stromal cells. Endocrinology 130:1318-1324). Noggin was shown to be expressed in condensing cartilage in mice, and mice genetically altered to lack noggin were found to have shorter but thicker limbs and multiple synarthroses (Brunet, L. J., et al. (1998) Noggin, cartilage morphogenesis, and joint formation in the mammalian skeleton. Science 280:1455-1457). Human mutations of the noggin gene have been shown to be associated with fibrodysplasia ossificans progressiva and synarthrosis syndromes (Semonin, O., et al. (2001) Identification of three novel mutations of the noggin gene in patients with fibrodysplasia ossificans progressiva. Am. J. Med. Genet. 102:314-317. Gong, Y., et al. (1999) Heterozygous mutations in the gene encoding noggin affect human joint morphogenesis. Nature Genet. 21:302-304).

Delivery of modified or wild-type noggin in a bone chamber reduced in-growth of new bone at four weeks in rats (Aspenberg, P., et al. (2001) The bone morphogenetic proteins antagonist noggin inhibits membranous ossification. J. Bone Mineral. Res. 16:497-500). Transgenic mice which over-expressed noggin under the control of the osteocalcin promoter exhibited diminished bone mineral density, reduced trabecular number and volume, reduced bone formation rate, but normal trabecular osteoclast surface with reduced osteoclast number (Devlin, R. D., et al. (2003) Skeletal over expression of noggin results in osteopenia and reduced bone formation. Endocrinology 144:1972-1978). Noggin delivered through a retroviral vector inhibited ectopic bone formation induced by demineralized bone matrix or vector-delivered BMP-4 (Hannallah, D., et al. (2004) Retroviral delivery of noggin inhibits the formation of heterotopic ossification induced by BMP-4, demineralized bone matrix, and trauma in an animal model. J. Bone Joint Surg. 86:80-91).

Demineralized bone matrix (DBM) and native bone morphogenetic protein (nBMP) are partially purified extracts of non-collagenous bone proteins that contain at least one endogenous BMP. BMP's belong to a family of growth factors described as bone morphogenic protein/non-collagenous protein (BMP/NCP or BMPs). Specifically BMP-2 and BMP-4 have been isolated therefrom, and are in the TGF-β family of proteins. However, DBM and nBMP also include enhancers and inhibitors of BMP activity.

For example, recently BBP has been disclosed as enhancing ossification caused by recombinant BMP. Further, BBP as used with BMP in vivo causes osteogenesis to occur faster, to a greater extent and with smaller amounts of rhBMP-2.

DBM and nBMP exhibit osteogenic potential, and can be used to enhance bone healing in a number of clinical situations. (Urist, M. R. (1965) Bone: Formation by autoinduction. Science 150:893-899; Reddi, A. H. and Huggins, C. (1972) Biochemical sequences in the transformation of normal fibroblasts in adolescent rats. Proc. Natl. Acad. Sci. U.S.A. 69:1601-31605 and Urist, M. R., et al. (1984) Purification of bovine bone morphogenetic protein by hydroxyapatite chromatography. Proc. Natl. Acad. Sci. U.S.A. 81:371-375. (Urist, M. R. Emerging Concepts of Bone Morphogenetic Protein. (1991) In: Fundamentals of Bone Growth: Methodology and Applications, A. D. Dixon, B. G. Sarnat, and D. A. N. Hoyte (eds.), pp. 189-198. (C.R.C. Press, Boston)). Because of the number of BMP-related proteins found in DBM and the complexity of their regulatory functions, it is likely that partially purified mixtures such as DBM and nBMP contain a number of molecules that affect the availability and activity of the BMPs. While recombinant BMPs are available, the cost of using minimally effective dosages of BMP has been a limiting factor in clinical use. Therefore, DBM and nBMP having increased osteogenic activity are desired.

Safe, effective and affordable compositions, devices and methods are desired to treat bone disorders (such as osteoporosis), bone injury (such as fracture healing of flat (e.g., membranous) and long (e.g., endochondral) bones, non-union fractures and reconstructive surgery), sites of knee/hip/joint repair or replacement surgery treating periodontitis, periodontal regeneration, alveolar ridge augmentation for tooth implant reconstruction, for example.

Further, the use of compositions and methods in combination with other methods for enhancing osteogenesis are desirable.

It may be desirable to improve DBM and nBMP by adding activators and substances which improve the kinetics or overall osteogenic potential of BMP action or by removing inhibitors of BMP action, for example.

Further, methods for removing inhibitors of BMPs, while not adversely effecting the osteogenic activity of BMPs in DBM (such as BMP-2, -4 and -7 (known as "osteogenin"), are desirable. Also desirable are DBM and/or rBMP which produces more bone per volume or weight than native DBM or nBMP obtained from non-processed DBM. Finally, methods which do not adversely effect the osteogenic potential of DBM are desirable.

SUMMARY OF THE INVENTION

In one aspect of the invention, it is desirable to increase the osteogenic activity of DBM or nBMP by reducing the levels of or removing inhibitors of osteogenic activity therefrom, and more specifically to remove inhibitors of BMP action therefrom.

In one aspect of the invention, an alkali-urea extraction may be used to substantially reduce the levels of or remove inhibitory proteins, including but not limited to noggin, in a water soluble extractate from DBM or nBMP.

The invention may include a method of systemic delivery or localized treatment with agents for maintaining bone homeostasis, enhancing bone formation and/or enhancing bone repair. The invention may include a method of systemic delivery or localized treatment with cells for maintaining bone homeostasis, enhancing bone formation and/or enhancing bone repair.

In one application of the invention, the method may be applied to induce the formation, local repair, effective bone homeostasis in bone related disorders, such as osteoporosis.

The invention may also include devices such as implants having coatings of substances or seeded with differentiated cells for inducing bone formation or enhancing bone repair. The invention may also include the application of substances or differentiated cells at a site where bone formation or bone repair is desired. For example, implants may include, but are not limited to pins, screws and plates that are used to immobilize a fracture, enhance bone formation or stabilize a prosthetic implant by stimulating bone formation or bone repair.

This invention is advantageous at least in that DBM or nBMP, for example may enhance osteogenesis and the activity of other osteogenic materials, such as BMP-2, BMP-4 or BMP-7. Therefore, lower doses of osteogenic materials may be used for clinical applications. This is significant at least in that clinical treatments may be more affordable. Further this invention is advantageous at least in that BBP may be used to further enhance the osteogenic potential of DBM and/or nBMP.

These, as well as other objects, features and benefits will now become clear from a review of the following detailed description of illustrative embodiments and the accompanying drawings.

BRIEF DESCRIPTION OF DRAWINGS

FIG. 1 is a radiogram of hindquarters of nude mice 28 days after implantation with 25 mg of either DBM (left) or extracted DBM (right). Ectopic bone formation is observed in all the specimens (see arrows; note areas of increased opacity above the femur).

FIG. 2 is a radiogram of hindquarters of nude mice 28 days after implantation with 25 mg of extracted DBM plus 25 mg of the water soluble fraction of the alkali-urea extractate. (Arrows indicate the site of implantation; material in the concentrated extractate has inhibited the osteogenic potential of the DBM.)

DETAILED DESCRIPTION

Figure 3:
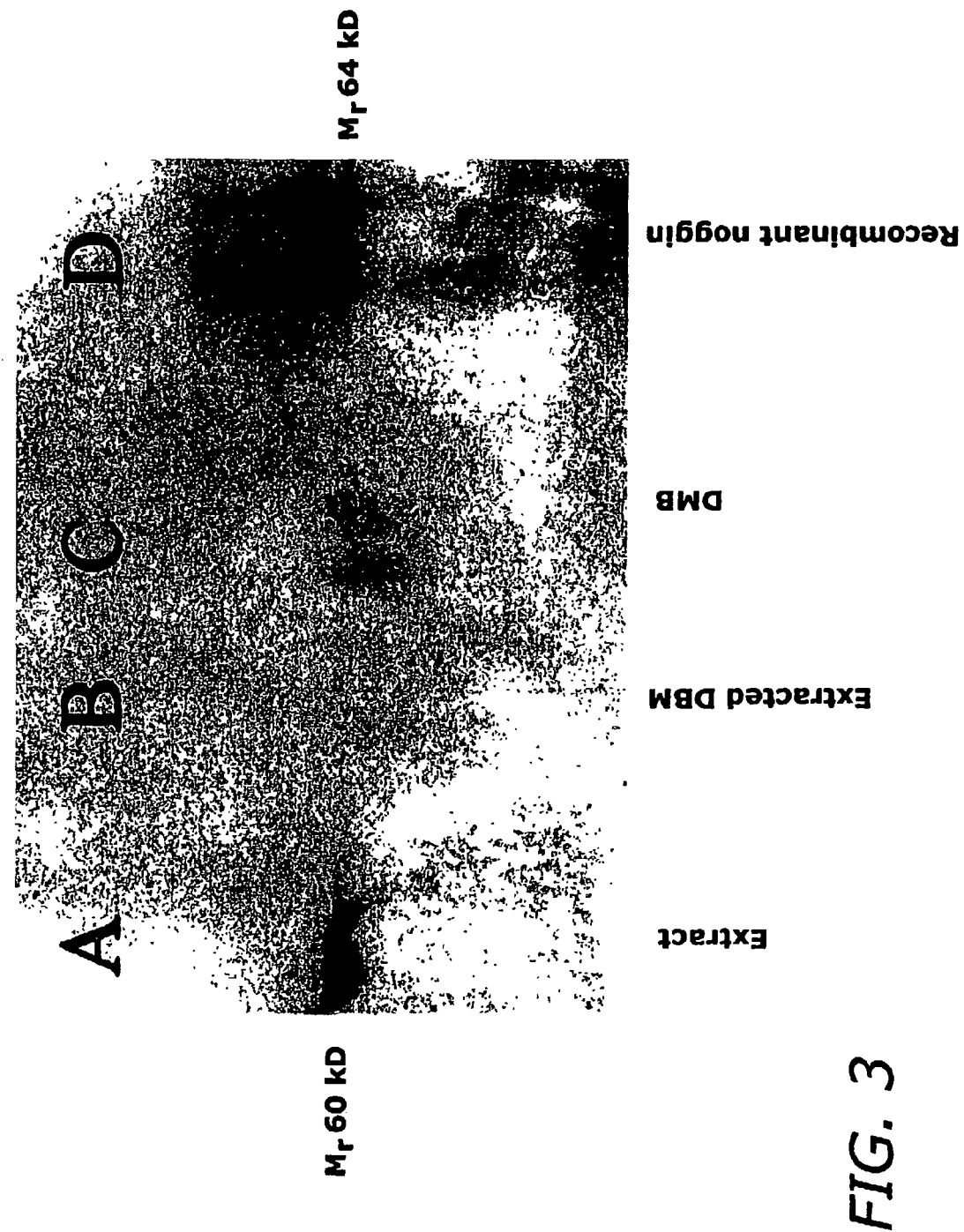
FIG. 3 is a Western blot for the detection of noggin in protein representing 2.5 mg of each test material. Lanes A: Water soluble fraction of the alkali-urea extractate of DMB; B: Alkali-urea extracted DBM; C: Untreated DBM; D: 1 µg recombinant noggin/Fc chimeric protein. (Noggin is present in the extractate and untreated DBM, but not the treated DBM. The arrow points to the recombinant noggin in lane D with an expected $M_r$ of 64 kD. Native noggin seen in lanes A, B, or C, is expected to have a $M_r$ of 60 kD.)

Demineralized bone matrix (DBM) and the native bond morphogenetic protein (nBMP) that is purified from it induce ectopic endochondral bone formation that can be used to enhance bond healing in a number of clinical situations. These materials are complex mixtures of numerous proteins and contain a number of the known bond morphogenetic proteins (BMPs) and, possibly, BMP-binding proteins or inhibitors of BMPs. Therefore, DBM-related materials with increased osteogenic activity are desired.

The present invention is related to agents such as DBM, nBMP and/or proteins and methods for maintaining bone homeostasis, enhancing osteogenesis to promote bone formation and/or enhancing bone repair.

One embodiment may include a method for making and a composition comprising DBM and/or nBMP extracted to remove or reduce the amount of non-osteogenic proteins (such as noggin). Extraction may be with a chaotropic solvent, such as urea in a concentration from about 1M to 4.5M, for example. Preferably DBM extraction should be undertaken in a way so as to not eliminate the osteoinductive activity of the DBM or nBMP therein.

Further, one embodiment may include a method for making and a composition comprising proteins, such as non-collagenous proteins from extracted DBM or nBMP as described above. A second extraction may be with one of a chaotropic solvent (for example, about 4M quandidine HCL, 6M urea), an ionic detergent (for example, about 1% sodium dodecylesulfate) or nondenaturing concentrations of acid (for example, about 1 to about 2M citric acid).

More specifically, embodiments of the invention may include the systemic and/or local application of agents for maintaining bone homeostasis, enhancing bone formation and/or enhancing bone repair. Clinical indices of a method or compounds ability to maintain bone homeostasis is evidenced by improvements in bone density at different sites through out the body as assessed, at least by DEXA scanning. Enhanced bone formation in a healing fracture is routinely assessed by regular X-ray of the fracture site at selected time intervals. More advanced techniques for determining the above indices, such as quantitative CT scanning may be used.

More specifically, embodiments of the invention may include the use of agents which stimulate osteogenesis. Embodiments of the invention may include the use of agents which induce the proliferation of precursor cells which subsequently differentiate into bone cells (osteoblasts), such as DBM and/or nBmp.

Embodiments of the invention may also include the use of agents which inhibit osteoclastic bone resorption. Agents which may be useful in this invention to effect osteoclastic bone resorption include, but are not limited to: bisphosphonates, selective estrogen receptor modulators, calcitonin, vitamin D and/or calcium supplementation. Embodiments of the invention may also include the use of agents which induce osteoblastic bone formation. Agents which may be useful in this invention include, but are not limited to PTH, sodium fluoride and growth factors, such as insulin-like growth factors I and II and transforming growth factor beta.

The in vivo models used to show the osteogenic effects of extracted DBM, nBMP or non-collagenous proteins have been used previously in demonstrating similar behaviors of other osteogenic compounds. In particular, in vivo models have previously been able to successfully predict the in vivo osteogenic effects of compounds such as BMP and insulin like growth factors (IGF). Specifically, it has been demonstrated that BBP enhances the osteogenic potential of BMP-2 in a mouse hindquarter assay. Demonstration of osteogenic effects of a compound in these in vivo models are necessary prior to trials that would demonstrate their effects in vivo humans.

Agents which may be useful in this invention to effect osteogenesis include, but are not limited to extracted DBM, nBMP and/or non-collagenous proteins alone or in combination with other osteogenic agents, such as BMP-2, BMP-4, BMP-7 or any portion of these peptides which are found to be active in effecting calcification or osteogenesis. Further, BPP may be added to enhance the osteogenic potential of BMP-2, for example.

Therapeutically Effective Dose.

A therapeutically effective dose of a agent useful in this invention is one which has a positive effect on a patient or desired effect in cells as measured by the ability of the agent to enhance calcification or osteogenesis, as described above. The therapeutically effective dose of each agent can be modulated to achieve the desired clinical effect, while minimizing negative side effects. The dosage of the agent may be selected for an individual application depending upon the route of administration, severity of the disease, age and weight of a patient, other medications the patient is taking and other factors normally considered by an attending physician, when determining an individual regimen and dose level appropriate for a particular patient. It is desirable at least that the extracted DBM, nBMP, or non-collagenous proteins may lead to a more active therapeutic material relative to the same weight or volume of native DBM or native BMP ("non-extracted"). The therapeutically effective dosage of DBM and nBMP substantially free of noggin may be determined to be less than that of DBM and nBMP including noggin.

Dosage Form.

The therapeutically effective dose of an agent included in the dosage form may be selected by considering the type of agent selected and the route of administration. The dosage form may include an agent in combination with other inert ingredients, including adjutants and pharmaceutically acceptable carriers for the facilitation of dosage to the patient, as is known to those skilled in the pharmaceutical arts.

Therapeutic formulations may be prepared for storage by mixing the agents having the desired degree of purity with optional physiologically acceptable carriers, excipients or stabilizers, in the form of lyophilized cake or aqueous solutions. Acceptable carriers, excipients or stabilizers are non-toxic to recipients at the dosages and concentrations employed, and include buffers such as phosphate, citrate, and other organic acids; anti-oxidants including ascorbic acid; low molecular weight (less than about 10 residues) polypeptides; proteins, such as serum albumin, gelatin or immunoglobulins. Other components can include glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The dosage form may be provided in a topical preparation (e.g., lotion, crème, ointment, transdermal patch, or the like) for dermal application. The dosage form may also be provided in preparations for subcutaneous (such as in a slow-release capsule), intravenous, intraparitoneal, intramuscular or respiratory application, for example.

In one embodiment, the dosage form may be an oral preparation (e.g., liquid, capsule, caplet or the like) which when consumed results in the elevated levels of the agent in the body. The oral preparation may comprise carriers including diluents, binders, time release agents, lubricants and disinigrants.

Any one or a combination of agents may be included in a dosage form. Alternatively, a combination of agents may be administered in separate dosage forms. A combination of agents may be administered concurrent in time such that there is exposure to at least two agents for treatment.

Additional Agents.

The invention may include treatment with an additional agent which acts independently or synergistically with extracted DBM, nBMP and/or DMP proteins to enhance osteogenesis and/or calcification. For example, DBM and/or nBMP having reduced levels of non-osteogenic proteins or peptides may be combined with BMP, BPP, bisphosphonates, hormone therapy treatments, such as estrogen receptor modulators, calcitonin, vitamin D, calcium supplementation, PTH (such as Forteo or teriparatide, Eli Lilly), sodium fluoride and/or growth factors that have a positive effect on bone, such as insulin-like growth factors I and II and transforming growth factor beta. Those skilled in the art would be able to determine the accepted dosages for each of the therapies using standard therapeutic dosage parameters, and reduced dosages of DBM and/or BMP where the effects of secondary agents are synergistic.

Figure 4:
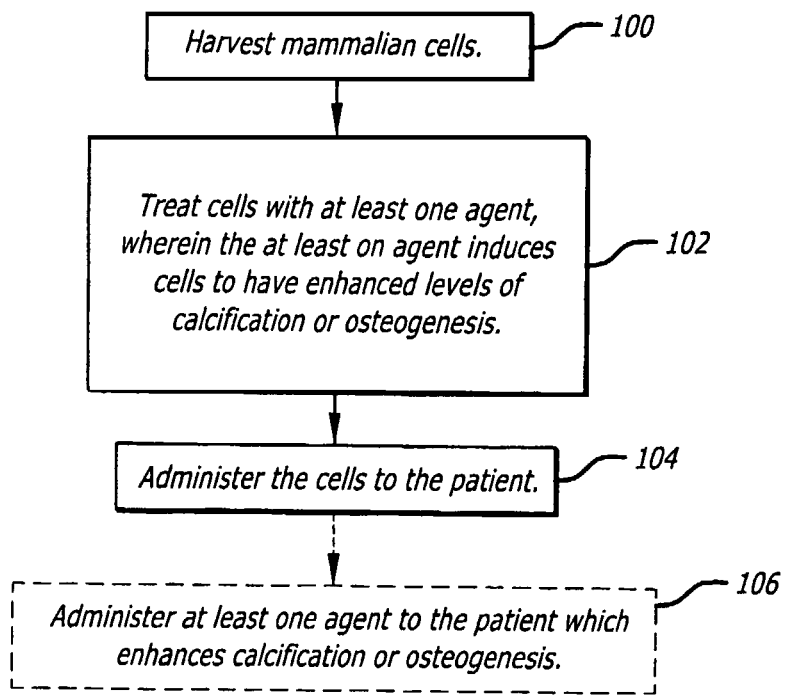
FIG. 4 is a flow chart of one method of the invention.

FIG. 4 depicts a flowchart of one method according to this invention. In this embodiment of the method, mammalian cells, such as mesenchymal stem cells can be harvested from a patient or a cell donor (100). The cells may be injected where bone formation or repair is desired, or first treated with at least one agent (such as extracted DBM, BMP or proteins) to induce osteogenesis or specifically osteoblastic differentiation (102). The cells may then be administered to a patient, such as systemically or at a selected site at which osteogenesis is desired (104). Additionally, the patent may by treated locally or systemically with at least one additional agent which effects osteogenesis, such as DBM and nBMP alone or in combination with BMP-2, BMP-4, BMP-7 or other osteogenic factors (106), or BPP to enhance the osteogenic activity of BMP-2, for example.

Figure 5A:
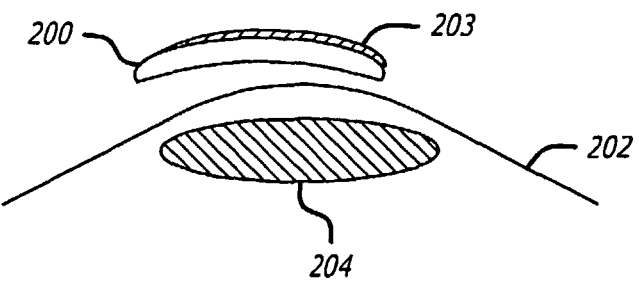
FIGS. 5 A & B are schematic depictions of two embodiments of the present invention.

FIGS. 5A & B depict two embodiments of the present invention. In FIG. 5A, the invention may include implants or grafts (200) for use in vivo comprising, a substrate having a surface (201), wherein at least a portion of the surface of the implant includes extracted DBM, nBMP and/or an extract of non-collagenous proteins recovered from DBM extraction (203) in an amount sufficient to induce osteogenesis, chondrogenesis, or calcification in the surrounding tissue, and the implant may include osteogenic cells expressing BBP and/or BMP. The implant may be shaped in the form of pins, screws, plates or prosthetic joints which may be placed in the proximity of, or in contact with a bone (202) that are used to immobilize a fracture, enhance bone formation, or stabilize a prosthetic implant by stimulating formation or repair of a site of bone removal, fracture or other bone injury (204).

Figure 5B:
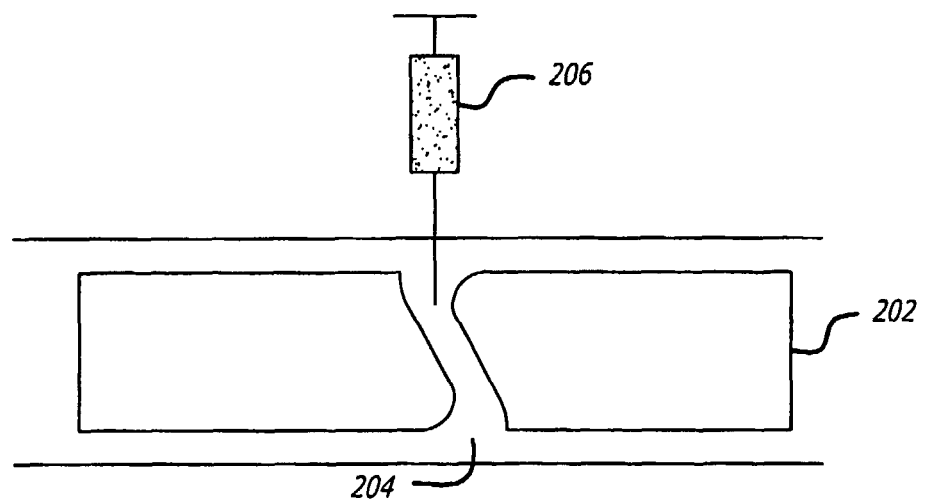

As shown in FIG. 5B, the invention may also include the in vivo or in vitro (such as on cultures of collagen or chondrocytes) or in vivo application of at least an extracted DBM and/or nBMP containing composition (206) in the proximity of or in contact with a bone (202), an implant (200) at a site of bone removal, fracture or other bone injury (204) where osteogenesis or calcification is desired. The extracted DBM, nBMP and/or an extract of non-callagenous proteins recovered from DBM extraction may be applied in combination with other agents such as BBP, BMP-2, BMP-4, BMP-7 or collagen cultures. For example: stem cells for treating bone related disorders in humans has also been examined. Infusion of osteoblastic progenitor stem cells from a healthy individual into a diseased individual has been shown to improve bone density in some osteogenic insufficient patients.

Figure 6:
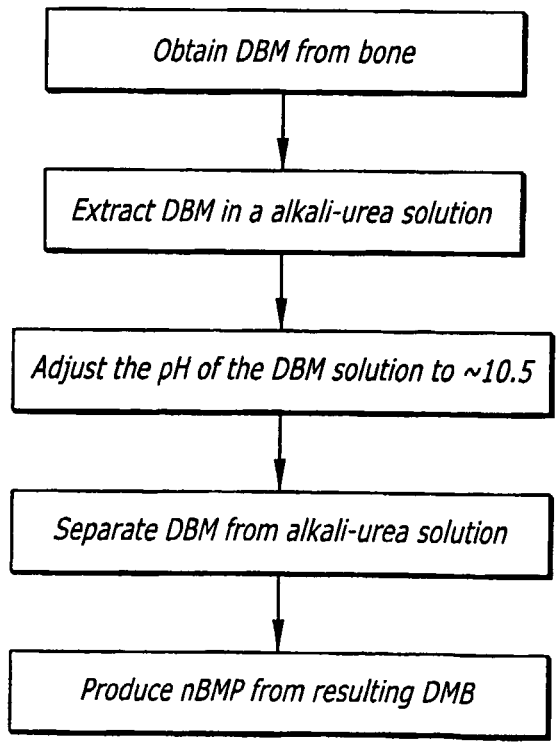
FIG. 6 is a flow chart of one method of the invention.

FIG. 6 depicts a flowchart of one method according to this invention. For example, DBM may be obtained from bone using methods known to those in the art. The DBM may be extracted in a alkali-urea solution, and the alkali-urea-DBM solution may be adjusted, such as to pH about 10.5. The DBM may be separated from the alkali-urea solution, and optionally, nBMP may be produced from resulting the DBM using methods known to those of skill in the art. The DBM or nBMP may be further extracted to derive non-collagenous proteins with osteogenic activity. The resulting DBM or nBMP may be used, such as for implanting in vivo at a site where bone formation is desired.

EXAMPLE 1

A series of studies were undertaken in which chemical extractions were tested for the potential to remove enhancers or inhibitors of BMP activity from DBM. One such treatment was an overnight extraction with alkali-urea, which was used to remove proteins from DBM based on the net charge of the proteins. The osteogenic activity of extracted DBM was compared to that of DBM to which an equal mass of concentrated extractate had been added.

Materials and Methods

Production Of Demineralized Bone Matrix.

Demineralized bone matrix (DBM) was prepared as described previously by Urist (Urist, M. R., Huo, Y. K., Brownell, A. G., Hohl, W. M., Buyske, J., Lietze, A., Tempst, P., Hunkapiller, M., and DeLange, R. J. (1984) Purification of bovine bone morphogenetic protein by hydroxyapatite chromatography. Proc. Natl. Acad. Sci. U.S.A. 81:371-375. Urist, M. R. Emerging Concepts of Bone Morphogenetic Protein. (1991) In: Fundamentals of Bone Growth: Methodology and Applications, A. D. Dixon, B. G. Sarnat, and D. A. N. Hoyte (eds.), pp. 189-198. (C.R.C. Press, Boston). Briefly, fresh bone was cleaned, ground, washed with water in the presence of protease inhibitors, defatted with 1:1 (v/v) chloroform:methanol, demineralized with 0.6 M HCl, washed again, and lyophilized.

Alkali-Urea Extraction Of Demineralized Bone Matrix.

DBM was extracted in a solution which had been prepared by adding equal volumes of 6 M urea and 0.1 M KOH. The pH of this solution was adjusted to 10.5 with HCl and the solution was made 2 mM N-ethylmaleimide (NEM), 0.1 mM benzamidine HCl, and 0.02% $NaN_3$. Ground DBM was left in this solution in the cold overnight with stirring. A proportion of 5 liters/kg was used. The pH of the solution was adjusted to 10.5 with 1M KOH at 0.5, 1, and 4 hours, but not subsequently. The following day the supernatant was removed by decanting and the remaining solid material was then washed with a large volume of water containing protease inhibitors in the cold overnight, and subsequently collected by filtration and lyophilized. The extracted supernatant was collected and dialyzed against 20 volumes of water in the cold with 2 changes over a 48 hour period. Dialysis tubing with a 6-8 kD molecular weight cut-off was employed (Spectropor from Spectrum Medical Industries, Laguna Hills, Calif.). The dialyzed supernatant was centrifuged at 10,000 rpm for 30 minutes at 4° C. in a Sorvall GSA rotor (Kendro Laboratory Products, Newtown, Conn.). The precipitate and supernatant were lyophilized separately. The water soluble fraction was used in subsequent experiments.

In Vivo Assay Of Osteogenic Activity.

The osteogenic activity of test materials were tested using an in vivo assay approved by the Sepulveda Animal Subjects Committee and the VA Greater Los Angeles Research and Development Committee. Male NIH Swiss-Webster nude mice aged 5 to 8 weeks were used (Taconic Farms, Germantown, N.Y.). Prior to the assay, the DBM to be tested was sorted through number 100 and number 20 wire sieves. Material with a particles size of 150 to 850 micrometers was placed in #5 gelatin capsules and sterilized by exposure to chloroform vapor. To conduct the assay, mice were anesthetized using 1% isoflurane delivered in oxygen at 2 l/min through a small animal anesthesia machine (VetEquip, Pleasanton, Calif.). Animals were affixed to a surgery board and the fur over the hindquarters was shaved. The skin was cleaned with 70% ethanol and a midline incision made over the spine adjacent to the hindquarters. Blunt dissection with scissors was used to expose the quadriceps muscle on one side. A small pouch was made in the muscle using the point of the scissors and the #5 capsule containing the test material was inserted into the pouch. The skin was then closed with three 11-mm Michel surgical clips and the animal returned to its cage for monitoring. After 28 days the animals were sacrificed and the hindquarter removed. Radiological examination of the specimens was accomplished using a small parts X-Ray cabinet (Faxitron, Wheeling, Ill.). Specimens were then placed in buffered formalin and submitted for routine processing for histological examination. Implants consisted of 25 mg of starting material DBM, 25 mg of extracted DBM, or 25 mg of extracted DBM plus 25 mg of concentrated water soluble extractate.

Electrophoresis And Western Blotting.

SDS polyacrylamide gel electrophoresis under non-reducing conditions and Western blotting were conducted employing standard equipment and the instructions provided by the manufacturer (BioRad, Hercules, Calif.). Noggin/Fc recombinant chimeric protein and goat anti-mouse noggin were obtained from R & D Systems (Minneapolis, Minn.). The primary antibody was used at final concentration of 0.075 µg/ml. The secondary antibody was donkey anti-goat IgG conjugated to alkaline phosphatase and was used at a 1:2500 dilution (Piece, Rockford, Ill.). Color development was accomplished with the BCIP/NBT with suppressor reagent from Pierce (Rockford, Ill.).

In order to determine the relative noggin content of the DBM starting material, extracted DBM, and the extractate, 400 µl of Laemmli sample buffer was added to 50 mg of each material. The samples were boiled, mixed vigorously, and briefly spun in a centrifuge. Aliquots of 20 µl, representing about 2.5 mg of material, were separated by SDS-PAGE electrophoresis. Parallel gels were run and stained with Coomassie blue in order to confirm equal loading.

Results

The Effect of Extractate on the Osteogenic Activity of DBM.

FIGS. 1 and 2 demonstrate radiologically the effect of an equal amount (25 mg) of water soluble extractate on the osteogenic activity of DBM. The results presented in FIG. 1 confirm and compare the osteogenic activity of DBM starting material (FIG. 1, two specimens on the left) and extracted DBM (FIG. 1, two specimens on the right). Both DMB and extracted DMB induced ectopic bone formation as can be seen in the large areas of calcification (shown at arrows). Histological examination confirmed that the calcification was associated with osteogenic bone formation and not simply dystrophic calcification.

The results presented in FIG. 2 show the effects of the water soluble extractate on the osteogenic potency of extracted DBM. No ectopic bone formation was observed in any of the four implants containing both extracted DBM (25 mg) and the water soluble fraction of the alkali-urea extractate (25 mg) (FIG. 2, all four specimens).

Demonstration of the Presence of Noggin, an Inhibitor of BMPs, in the Water Soluble Extractate.

FIG. 3 shows a Western blot of DBM, extracted DBM, extractate, and recombinant noggin/Fc chimeric protein developed with an anti-mouse noggin primary antibody. The $M_r$ of the noggin/Fc chimeric protein is 60 kD whereas the expected $M_r$ of native (dimeric) noggin is 64 kD (Smith, W. C., et al. (1993). Secreted noggin protein mimics the Spemann organizer in dorsalizing *Xenopus* mesoderm. Nature 361:547-549). This study confirms the presence of noggin, a known inhibitor of BMP activity, generally, in the water soluble fraction of the alkali-urea extractate of DBM (FIG. 3, lane A) at a much higher level than in the DBM starting material (FIG. 3, lane C) and especially the extracted DBM (FIG. 3, lane B).

While the specification describes particular embodiments of the present invention, those of ordinary skill can devise variations of the present invention without departing from the inventive concept.

The invention claimed is:

1. A composition comprising a demineralized bone matrix having been extracted with a chaotropic solvent at an alkaline pH, wherein the demineralized bone matrix after extraction contains at least one bone morphogenetic protein and has osteoinductive activity, and wherein the demineralized bone matrix after extraction has fewer non-osteogenic proteins than native demineralized bone matrix.

2. The composition of claim 1, wherein the chaotropic solvent comprises urea in a concentration between about 1M to about 4.5M.

3. The composition of claim 1, wherein the chaotropic solvent comprises urea in a concentration of about 6M and about 0.1M KOH.

4. A method for producing demineralized bone matrix comprising the steps of:
    (a) obtaining demineralized bone matrix from bone tissue;
    (b) extracting the demineralized bone matrix with a chaotropic solvent at an alkaline pH;
    (c) isolating the resulting demineralized bone matrix
    wherein the demineralized bone matrix after extraction contains at least one bone morphogenetic protein and has reduced levels of osteogenic inhibitory factors.

5. The composition of claim 1, wherein the chaotropic solvent is an alkali-urea solution.

6. The composition of claim 1, wherein the alkaline pH is about 10.5.

7. The method of claim 4, wherein the chaotropic solvent is an alkali-urea solution.

8. The method of claim 4, wherein the alkaline pH is about 10.5.

* * * * *